United States Patent
Sjöholm

[11] Patent Number: 6,157,855
[45] Date of Patent: Dec. 5, 2000

[54] MEDICAL APPARATUS

[75] Inventor: Gösta Sjöholm, Ekerö, Sweden

[73] Assignee: Siemens-Elema AB, Solna, Sweden

[21] Appl. No.: 09/285,095

[22] Filed: Apr. 2, 1999

[51] Int. Cl.[7] ............................................. A61B 5/05
[52] U.S. Cl. ............................................................ 600/427
[58] Field of Search .................................. 600/407, 424, 600/427

[56] References Cited

U.S. PATENT DOCUMENTS

| | | |
|---|---|---|
| 5,230,338 | 7/1993 | Allen et al. . |
| 5,357,550 | 10/1994 | Asahina et al. . |
| 5,377,678 | 1/1995 | Dumoulin et al. . |
| 5,433,198 | 7/1995 | Desai . |
| 5,447,164 | 9/1995 | Shaya et al. . |
| 5,469,857 | 11/1995 | Laurent et al. . |
| 5,619,995 | 4/1997 | Lobodzinski . |
| 5,638,819 | 6/1997 | Manwaring et al. . |
| 5,640,967 | 6/1997 | Fine et al. . |
| 5,730,129 | 3/1998 | Darrow et al. . |
| 5,740,808 | 4/1998 | Panescu et al. . |

*Primary Examiner*—William E. Kamm
*Attorney, Agent, or Firm*—Schiff Hardin & Waite

[57] ABSTRACT

A medical apparatus has an input unit with a number of input terminals to which at least one measuring and/or therapeutic elements is connectable and a display unit for displaying currently connected measuring and/or therapeutic elements. An imaging system produces an image of the cavity or the environment in which the measuring and/or therapeutic elements are situated, together with images of the measuring and/or therapeutic elements. A graphic indication of the currently connected measuring and/or therapeutic elements us superimposed on the image from the imaging system.

8 Claims, 2 Drawing Sheets

MEDICAL APPARATUS

BACKGROUND OF THE INVENTION

1. Field of the Invention

The present invention relates to a medical apparatus of the type having an input unit with a number of input terminals for the connection of intracorporeal measuring and/or therapeutic elements (generically referred to hereinafter as "patient interactive elements"), and a display device for displaying the currently connected patient interactive elements.

2. Description of the Prior Art

An apparatus for measuring electrical activity in the heart using patient interactive elements in the form of a number of electrode poles disposed on implanted intracardiac catheters is known from European Application 0 614 678. This apparatus senses and shows on a display unit the currently connected electrode poles as well as the electrode poles which are in contact with heart tissue.

SUMMARY OF THE INVENTION

An object of the present invention is to provide a medical apparatus which conveys more information about the patient interactive elements than is available from known apparatuses.

The above object is achieved in accordance with the principles of the present invention in a medical apparatus having an input unit with a number of input terminals and a number of intracorporeally introducible patient interactive elements which are respectively connectable to the input terminals. Means are provided for identifying which patient interactive terminals are connected, and an imaging system is provided which generates an image of an internal environment of a patient at which the patient interactive elements are disposed. This image will also contain images of any of the patient interactive elements which are within that environment. A processor is supplied with the image from the imaging system and locates each of the patient interactive elements which are contained within this image. The processor is also supplied with the identification of the connected patient interactive elements, and generates an output image comprising the image provided by the imaging system with identifiers superimposed thereon which visually differentiate between images of any of the patient interactive elements contained within the image which are connected to input terminals, and images of any patient interactive elements which are not connected. This output image is displayed on a display unit.

The inventive medical apparatus thus presents an overview of the currently connected elements in a readily intelligible manner by providing a unit which generates an image, for display, of the intracorporeal environment in which the patient interactive element is disposed superimposed on which is an image showing the currently connected patient interactive elements. This greatly facilitates the work of the operator, usually a physician, performing the measurement or therapy using these elements.

In an embodiment of the medical apparatus according to the invention, measurements made by measuring elements of the patient interactive elements are also arranged to be displayed. An overview of currently connected measuring and/or therapeutic means which constitute the patient interactive elements of the apparatus, the location of these elements inside the patient's body and the magnitude of the parameter measured by the connected measuring elements, is thereby provided. This is a significant advantage for the operator. The image displayed can be both text and graphic information, preferably in the form of mixed graphic information and text information on a single monitor.

In another embodiment of the medical apparatus according to the invention, the patient interactive elements include measuring elements devised to measure ECG signals, blood pressure or oxygen pressure. The medical apparatus can also advantageously be devised to permit the monitoring of these parameters over time for a patient.

In a further embodiment of the medical apparatus according to the invention, the patient interactive elements include therapeutic elements which may be a heart stimulator or ablation equipment. The heart stimulator can be of a type used, for example, for electrophysiological examinations and which delivers a series of pulses to the heart and to ablation equipment of the kind used for electrophysiological therapy.

In another embodiment of the medical apparatus according to the invention, a switching device is arranged to establish connections, in an selected manner, between input and output terminals of the apparatus and/or between input terminals and patient interactive elements, thereby providing a great flexibility in the function and use of the apparatus.

In a further embodiment of the apparatus according to the invention, a touch screen is arranged to show the input and output terminals of the apparatus, the desired connections between these being achieved when the screen is selectively touched. Connections between input and output terminals can therefore be achieved in a convenient manner. The currently established connections can be therefore readily displayed to also supply an overview of these currently established connections.

A communications unit may also be included in the medical apparatus of the present invention, arranged to communicate with a remote system via a communications link in the form of e.g. an electric cable, an optical link or a telemetric link. The apparatus can be controlled from the remote system, which for example may include computer equipment such as a PC, via the communications link and communications unit. The communications unit can be devised to permit acquisition of measurement data from the apparatus over the input terminals. The remote system can then be adapted for the processing and analysis of the acquired data and for the displaying of processed and acquired data on the display device.

DESCRIPTION OF THE PREFERRED EMBODIMENTS

Figure 1:
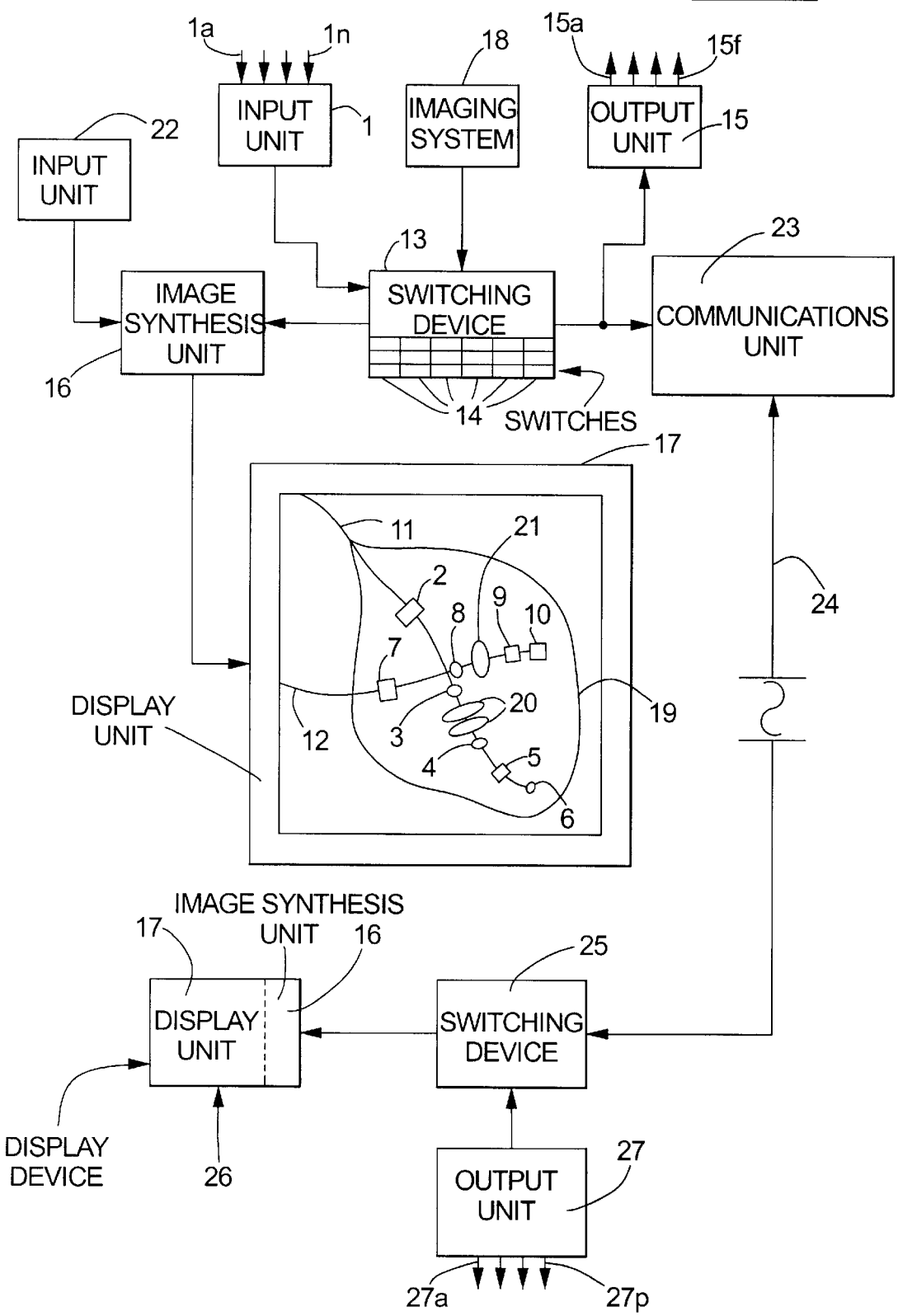
FIG. 1 is a schematic block diagram of a first embodiment of a medical apparatus according to the present invention.

Referring to FIG. 1, a first embodiment of the medical apparatus according to the present invention is shown with an input unit 1 having a number of input terminals 1a . . . 1n. A number of intracorporeally insertable patient interactive elements, here in the form of electrode poles 2 . . . 10 on catheters 11 and 12, are individually connected to corresponding input terminals 1a . . . 1n. The input unit 1 also contains input electronics, such as an amplifier for amplifying input signals applied to these input terminals 1a . . . 1n; and one or more of a number of processors and software for other appropriate signal processing.

The output of the input unit 1 is connected to a switching device 13. This switching device 13 is a switchbox with switches 14 to permit selected interconnection of the input terminals 1a . . . 1n of the input unit 1 and number of output terminals 15a . . . 15f of an output unit 15. This arrangement conveniently enables, for example, a number of the electrode poles 2 . . . 10 to be mutually exclusively switched to use the same recording, storage or analysis devices (not shown) which may be connected to the output terminals 15a . . . f.

An image synthesis unit 16 is provided in operable connection with a display unit 17 to control the display of images on that display unit 17. The switching device 13 is also operably connected to the image synthesis unit 16 to provide information to that unit 16 to identify which input terminals 1a . . . 1n are currently connected via the switches 14 to output terminals 15a . . . 15f. This makes it possible for the display of currently connected electrode poles 2 . . . 10 to be made on the display unit 17, as will be more fully described below.

An imaging system 18, such as an X-ray machine, ultrasound equipment or equipment for imaging by mapping, is also connected for supplying image signals for transmission, via the switching device 13, to the image synthesis unit 16 where it is processed before being passed to the display unit 17, producing on the display unit 17 an image of the cavity or environment, e.g. an internal organ such as the heart, in which one or more measuring and/or therapeutic elements is/are situated.

The imaging system 18 is operated so that the image also includes an image of the patient interactive elements 2 . . . 10 together with the associated electrode catheters 11,12. The image synthesis unit 16 is adapted to analyze the image to identify within that image the electrode poles 2 . . . 10 of the catheters 11,12 and to insert into the image displayed on the display unit 17 a visual identifier to differentiate between those electrode poles 2 . . . 10 which are and those which are not currently connected to the output unit 15 dependent on the output from the switching device 13, as will be described more fully below.

As an example, FIG. 1 shows the display unit 17 displaying the image from the imaging system 18 containing two electrode catheters 11,12, inserted into the heart 19 of a patient. Each catheter 11,12 has a number of patient interactive elements, here in the form of electrode poles 2 . . . 6 and 7 . . . 10 respectively. The image synthesis unit 17 has superimposed on this image a symbolic indication of those currently connected electrode poles. Of these, the electrode poles 2,5 on the catheter 11 and 7,9,10 on the catheter 12 are connected to the output unit 15 and are designated with squares in the image on the display unit 17. The other electrode poles 3,4,6 on the catheter 11 and 8 on the catheter 12 are not connected and remain displayed as imaged by the imaging system 18. As FIG. 1 shows, the display unit 17 supplies an overview of the location in the heart 19 of both connected electrode poles 2,5,7,9,10 and disconnected electrode poles 3,4,6,8. Also shown within the display on the display unit 17 are radio-opaque markers 20,21 which are included on the electrode catheters 11,12 and usable as references by the synthesis unit 16 when identifying the electrode poles 2 . . . 10 within the image supplied by the imaging system 18.

To achieve this superimpositioning the image synthesis unit 16 is adapted to locate each electrode pole 2 . . . 10 within the image supplied by the imaging system 18 and to assign to each of the so located electrode poles 2 . . . 10 a reference number to uniquely identify the electrode pole of the image with an input terminal 1a . . . 1n.

The location of the electrode poles 2 . . . 10 within the image may be done automatically by the synthesis unit 16 using standard image processing algorithms to identify the pixels of the image from the imaging system 18 that correspond to the electrode poles 2 . . . 10 (for example by identifying those pixels above a certain intensity and comparing clusters of so identified pixels with a template pixel formation representative of an electrode). The synthesis unit 16 may be further adapted to automatically correlate the image of an electrode pole 2 . . . 10 with the physical electrode pole 2 . . . 10. To achieve this the image synthesis unit 16 processes the image to locate each pole 2 . . . 10 relative to a known position on the corresponding electrode catheter 11,12, for example its tip or preferably markers 20,21 when present, as located within the image by the synthesis unit 16. Using information on the physical connection of electrode pole 2 . . . 10 to input terminal 1a . . . 1n (such as may be supplied by the input unit 1 or in some other way predefined) the image synthesis unit 16 can automatically make the assignment of the reference number.

Alternatively, once the electrode poles 2 . . . 10 have been identified within the image from the imaging system 18 the assignment of a reference number may then be done manually using a user input device 22 such as a computer keyboard and/or mouse connected to the synthesis unit 16. Here a user may be required to enter an input terminal reference number as the synthesis unit 16 operates the display unit 17 to display images in which each located electrode pole 2 . . . 10 is highlighted in turn.

Indeed, even the location may be done manually by adapting the synthesis unit 16 to register the locations within the image from the imaging system 18 and displayed on the display unit 17 that are identified via the user input device 22 as being an electrode pole 2 . . . 10.

Once the electrode poles 2 . . . 10 have been identified within the image and the reference numbers assigned the synthesis unit 16 then uses the information supplied to it from the switching device 13 to identify the currently connected poles 2,5,7,9,10 and to superimpose over the pixels within the image which represent the connected poles 2,5,7,9,10 a square symbol. The so formed superimposed image is then passed to the display unit 17 for display.

The display unit 17 can also be arranged to display visual representations of signals or measurement values which are derived from signals input at one or more of the input terminals 1a . . . 1n and passed from the input unit 1 to the image synthesis unit 16 via the switching device 13. The image produced on the display unit 17 thereby provides the operator with an even more detailed information overview.

A communications unit 23 is further provided to communicate with remote equipment via a communications link 24 in the form of e.g. an electric cable, optical link or telemetry link. This remote equipment can contain a second switching device 25 and a display device 26 which has incorporated within it an image synthesis unit 16 and a display unit 17. The medical apparatus can accordingly be operated remotely via the communications link 24 and the communications unit 23, an important advantage in certain applications such as patient monitoring.

The second switching device 25 and the display device 26 can be advantageously implemented within computer equipment, such as a PC, the medical apparatus then being operated with the computer's normal controls, such as a keyboard and mouse, which controls also serve as the user interface 22. Here, the function of the switching device is advantageously performed by the computer's control unit. The computer equipment can additionally or alternatively be used for acquiring, storing, processing and analyzing data from the electrode poles 2 . . . 10.

The display device 26 can alternatively be a touch screen arranged to display a representation of the input terminal 1a . . . 1n of the input unit 1 and the output terminals 15a . . . 15f the output unit 15 the desired connections between these terminals then being achieved when the operator selectively touches inter-terminal parts of the screen. This accordingly eliminates the need for user accessible switches 14 within the switching device 25. Here, the display device is also arranged to display established connections.

The display device 26 may also be used to replace the separate image synthesis unit 16, display unit 17 and, as appropriate, the switching device 13.

The remote equipment can also incorporate a second output unit 27 with a number of output terminals 27a . . . 27p.

The patient interactive elements 2 . . . 10 may include therapeutic elements, such as a heart stimulator of the kind which emits a series of pulses for use in e.g. electrophysiological examinations, or ablation equipment used for electrophysiological treatment. The patient interactive elements 2 . . . 10 may additionally or alternatively include measuring elements, such as ECG equipment, sphygmomanometers or devices for measuring partial oxygen pressure.

Figure 2:
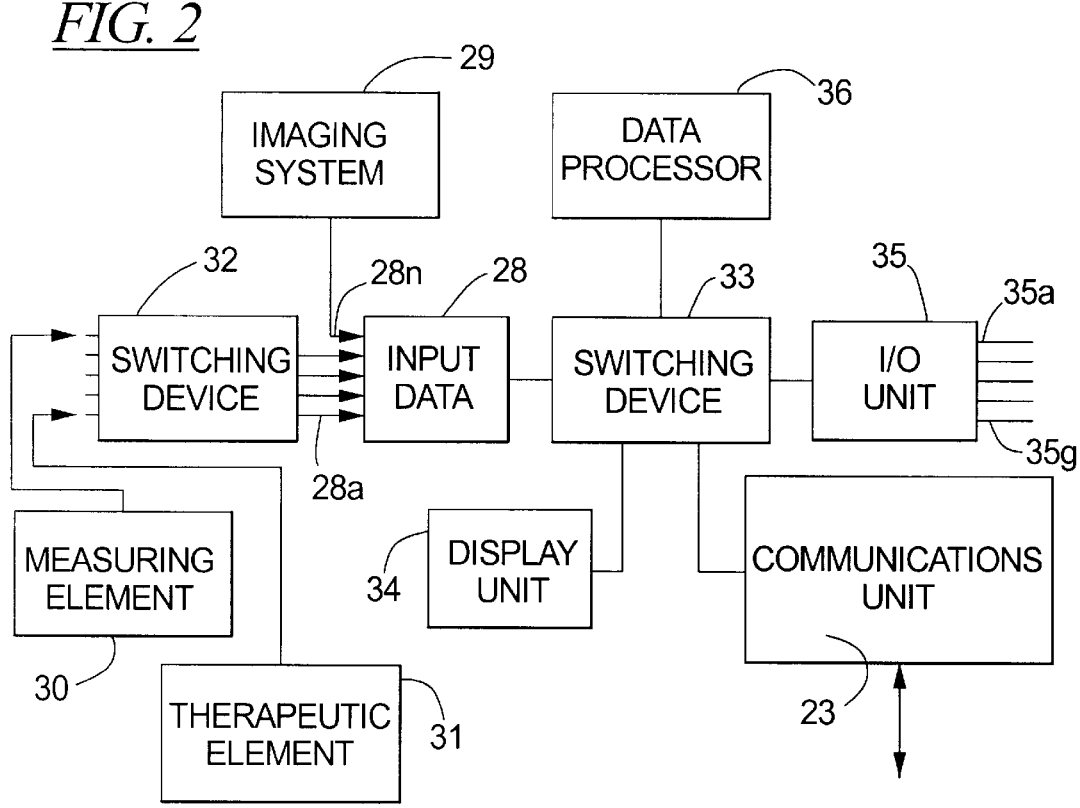
FIG. 2 is a schematic block diagram of a second embodiment of a medical apparatus according to the present invention.

FIG. 2 shows a second embodiment of the apparatus according to the present invention in which an input unit 28, having input terminals 28a . . . 28n, is connected to directly receive image in formation from an imaging system 29 depicting an interior portion of a patient's body and containing images of measuring and therapeutic elements 30,31. The measuring elements 30 and therapeutic elements 31 constitute user interactive elements a connection of which is to be monitored, which are connected to the input unit 28 through a switching device 32, similar in construction and operation to the switching device 13 of FIG. 1. The switching device 32 is operable to selectively establish connections between the elements of the measuring and therapeutic elements 30,31 and to output to the input unit 28 a signal indicating the currently connected patient interactive elements. The input unit 28 is adapted to analyze the image from the imaging system 29 to identify the patient interactive elements within the image and to generate an image depicting the information from the imaging system 29 superimposed with a visual identifier of the currently connected elements, in a manner as described above, and to output this composite image to a switching device 33. Depending on the settings of the switching device 33 the image may be displayed on a display unit 34 or sent, via a communications unit 23 to remote equipment (not shown). Information, such as measurement values or control signals, may also be passed to and from the connected measuring and therapeutic means 30,31 via the switching unit 33 and an input/output unit 35, having terminals 35a . . . 35g. An internal data processor 36 is also switchably connected via the switching device 33 to receive and process information from connected measuring and therapeutic elements 30,31.

Figure 3:
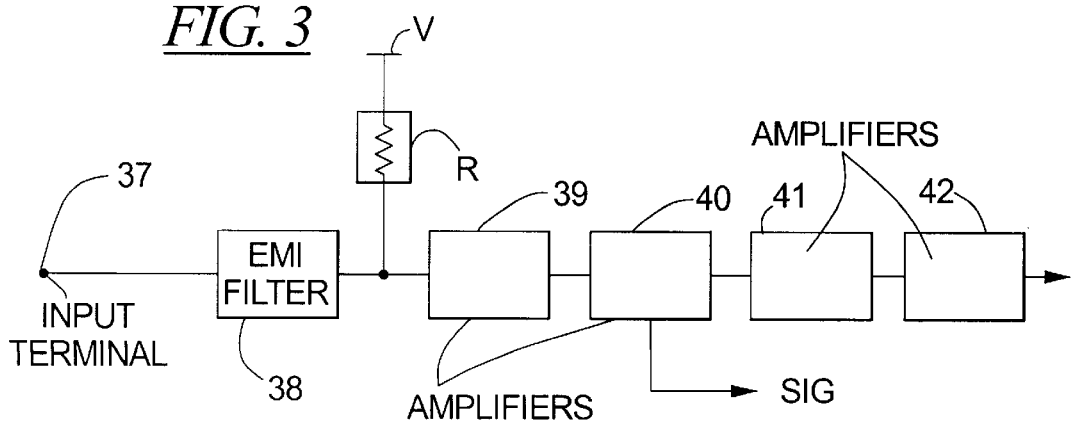
FIG. 3 is a schematic of a circuit diagram depicting part of an electric circuit associated with an input terminal of an input unit of the present invention.

The input units 1,28 may contain electric circuitry to enable an automatic detection of connected patient interactive elements to be made, for example by monitoring each terminal to determine whether it is open circuit (i.e. not connected). An input unit which is suitable for use in the present invention is described in European Application 0 614 678. FIG. 3 shows a circuit diagram of part of such an input unit and depicts just one input terminal 37.

As illustrated in FIG. 3, a so-called EMI filter 38 is provided at each input to protect against external interference, followed by a number of essentially identical amplifier stages 39, 40, 41, 42 for successive amplification of a signal at the input terminal 37.

If the input terminal 37 is not connected to an electrode pole or when it is connected to an electrode pole not in contact with the heart, i.e. when this input is open and is passing no current, the voltage V causes the input to go to a high level via the resistor R. This high level signal is amplified in the amplifiers 39 and 40 and used to indicate no connection (SIG). When the input terminal 37 is connected to an electrode pole in connection with the heart, the input is lowered to a low level (preferably, zero level), and the corresponding low signal from the amplifiers 39 and 40 is used to indicate a connection (SIG). In this manner, an automatic sensing of the poles connected to input terminals and to the heart is achieved.

This sensed connectivity may be used instead of the signal from the switching device 32 to provide the information which is used in the graphical identification of currently connected patient interactive elements. The connectivity signal (SIG) from the input unit 37 may also be used to generate a warning signal, usefully in the form of a graphic superimposed on the image of the appropriate electrode on the displayed image, to indicate those electrode poles which are currently connected to the input terminals but which are not connected to the heart.

For example, with reference to FIG. 2, the signal from the switching device 32 that indicates whether a measuring or therapeutic elements 30,31 is connected to a particular input terminal, for example 28a, may be compared with the open or closed circuit signal (SIG) generated by that terminal 28a detected using the circuit of FIG. 3. If an open circuit is detected from the signal (SIG) from amplifier 40 but the switching device 32 indicates a connection then a warning graphic is superimposed on the image of the electrode from the imaging system 29.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical apparatus comprising:

an input unit having a plurality of input terminals;

a plurality of intracorporeally introducible patient interactive elements respectively connectable to said input terminals;

means for identifying connected patient interactive elements;

an imaging system which provides a n image of an internal environment of a patient at which said patient interactive elements are disposed, said image also containing images of any of said patient interactive elements which are disposed in said environment;

a processor supplied with said image from said imaging system, which processes said image to locate said patient interactive elements within said image, to correlate any elements located in said image with said connected patient interactive elements and to generate an output image comprising said image provided by said imaging system with identifiers superimposed thereon which visually differentiate between images of any patient interactive elements which are connected and images of any patient interactive elements which are not connected; and a display connected to said processor for displaying said output image.

2. Apparatus as claimed in claim 1 wherein said patient interactive elements comprise measuring elements for producing a measurement signal having a magnitude and wherein said display displays a representation of said magnitude.

3. Apparatus as claimed in claim 1, further comprising a plurality of output terminals; and switching means connected between said input terminals and said output terminals for connecting, in a selected fashion, said input terminals with said output terminals.

4. Apparatus as claimed in claim 3 wherein said display comprises a touch screen connected to said switching means and operating said switching means to establish said selected connection by touching a specified location on said touch screen.

5. Apparatus as claimed in claim 1, further comprising switching means connected between said input terminals and said patient interactive elements for connecting, in a selected fashion, said input terminals with said elements.

6. Apparatus as claimed in claim 5 further comprising a communications unit for producing a communication link between said switching means an extracorporeal remote apparatus.

7. Apparatus according to claim 1 wherein said input unit identifies any of said input terminals which are connected to patient interactive elements.

8. Apparatus as claimed in claim 1 further comprising a communications unit for producing a communication between said processor and an extracorporeal remote apparatus.

* * * * *